(12) United States Patent
Chow

(10) Patent No.: US 8,143,559 B2
(45) Date of Patent: Mar. 27, 2012

(54) HEATING PAD WITH TEMPERATURE CONTROL AND SAFETY PROTECTION DEVICE

(75) Inventor: Kwok Wai Chow, Sheung Shui (HK)

(73) Assignee: Advance Thermo Control, Ltd., Hong Kong (HK)

( * ) Notice: Subject to any disclaimer, the term of this patent is extended or adjusted under 35 U.S.C. 154(b) by 282 days.

(21) Appl. No.: 12/551,938

(22) Filed: Sep. 1, 2009

(65) Prior Publication Data

US 2011/0049128 A1 Mar. 3, 2011

(51) Int. Cl.
*H05B 1/02* (2006.01)
(52) U.S. Cl. ........ 219/494; 219/212; 219/497; 219/481; 219/507
(58) Field of Classification Search .............. 219/497, 219/501, 504, 505, 212, 507; 323/235
See application file for complete search history.

(56) References Cited

U.S. PATENT DOCUMENTS

| 4,413,170 | A |  | 11/1983 | Val et al. |
| 5,057,674 | A |  | 10/1991 | Smith-Johannsen |
| 5,369,247 | A |  | 11/1994 | Doljack |
| 5,420,397 | A |  | 5/1995 | Weiss et al. |
| 5,422,461 | A |  | 6/1995 | Weiss et al. |
| 5,451,747 | A |  | 9/1995 | Sullivan et al. |
| 5,748,429 | A |  | 5/1998 | Peterson |
| 5,861,610 | A |  | 1/1999 | Weiss |
| 6,310,332 | B1 | * | 10/2001 | Gerrard ........................ 219/505 |
| 6,492,629 | B1 |  | 12/2002 | Sopory |
| 6,703,593 | B2 |  | 3/2004 | Sopory |
| 6,713,733 | B2 |  | 3/2004 | Kochman et al. |
| 6,958,463 | B1 |  | 10/2005 | Kochman et al. |
| 7,138,611 | B2 |  | 11/2006 | Yang |
| 7,180,037 | B2 |  | 2/2007 | Weiss |
| 2005/0247700 | A1 |  | 11/2005 | Kochman et al. |

FOREIGN PATENT DOCUMENTS

| DE | 3524933 | 1/1987 |
| EP | 0427433 | 10/1990 |
| JP | 1143114 | 6/1989 |
| JP | 2001025159 | 1/2001 |

* cited by examiner

*Primary Examiner* — Mark Paschall
(74) *Attorney, Agent, or Firm* — Boyle Frederickson, S.C.

(57) ABSTRACT

A heating pad is provided. The heating pad includes a heating element and a control circuit operatively connected to the heating element for providing a predetermined level of power thereto. An isolation device interconnects a power source to the control circuit. The isolation device has a first open configuration preventing transmission of electrical power therethrough and a second closed configuration allowing transmission of electrical power therethrough. The control circuit terminates power to the heating element in response to the heating element exceeding a first temperature limit. The isolation device moves from the closed configuration to the open configuration in response to the heating element exceeding a second temperature limit.

16 Claims, 3 Drawing Sheets

HEATING PAD WITH TEMPERATURE CONTROL AND SAFETY PROTECTION DEVICE

FIELD OF THE INVENTION

This invention relates generally to heating pads, and in particular, to a heating pad with a temperature control and safety protection device that has dual independent electronic hardware circuitries for preventing overheating of the heating pad.

BACKGROUND AND SUMMARY OF THE INVENTION

Heating pads are often used to keep individuals or certain muscles of an individual warm. Typically, a heating pad includes first and second sheets of cloth material having a heating structure captured therebetween. The heating structure includes a heating core wire connectable to an electrical power source through a controller. The controller allows a user to vary the magnitude of the electrical power provided to the heating core wire, and hence, to control the heat dissipated by the heating core wire and the temperature of the heating pad.

The heating core wire is contained in an insulation sheath that is protected by a woven screen. In normal use, it is intended for the heating pad to be spread out over a large surface area in order for the whole surface to dissipate the heat generated by the heating core wire. It can be appreciated that the maximum temperature reached by the heating core wire must be below the melting point of the insulation. However, the risk of a heating pad overheating may be significant in those situations when the heating core wire is electrically coupled to the electrical power source and the heating pad is folded onto itself so as to prevent the heat generated by the heating core wire to escape. In such a situation, a first layer of the folded heating pad may heat an adjacent layer (and vice versa) to such point as to cause the heating pad to reach a temperature that is capable of starting a fire. It is noted, however, that the insulation about the heating core wire must melt before the cloth layers of the heating pad begin to char and a fire starts.

In order to prevent the possibility of a fire starting due to the overheating of the heating pad, most heating pads incorporate a protective circuit. By way of example, Weiss et al., U.S. Pat. No. 5,422,461 discloses an electrical feedback safety circuit and a semiconductor switching system to control power to a heating element of the Positive Temperature Co-efficient "PTC" type that requires a safe operation condition in the event of an open or short circuit. An integrated circuit is used to signal a solid state switch to time the on and off proportion of the AC electric power to a flexible PTC heating element in order to control the temperature. Since the PTC element has the property of increased electrical resistance with increased temperature, the natural effect of increasing temperature is to throttle down and limit the current draw. The ability to control the temperature of the heater, by current control or time proportioned power control is improved. The power control level is affected externally by a heat scale setting via up-down key pad or rotary potentiometer and internally by the feedback safety circuit.

While functional for its intended purpose, the feedback safety circuit disclosed in the '461 patent has certain disadvantages. For example, the circuit includes two triacs which are both controlled by a single microprocessor. In the event the microprocessor fails, both triacs will be rendered inoperable. Further, triacs are relatively costly components. Incorporating two triacs into the design of the feedback safety circuit significantly increases the costs associated with the heating pad. As such, it is highly desirable to provide a temperature control and safety protection device for a heating pad that overcomes the disadvantages of the prior art.

Therefore, it is a primary object and feature of the present invention to provide a heating pad with a temperature control and safety protection device that has dual independent electronic hardware circuitries for preventing overheating of the heating pad.

It is a further object and feature of the present invention to provide a heating pad with a temperature control and safety protection device that is less expensive to manufacture than prior devices.

It is a still further object and feature of the present invention to provide a heating pad with a temperature control and safety protection device that shuts off the heating pad if a first, upper temperature limit is reached and that blows a fuse if a second, higher temperature limit is reached.

In accordance with the present invention, an improvement for heating pad having a heating element is provided. The improvement includes a control circuit operatively connected to the heating element for providing a predetermined level of power thereto. An isolation device is operatively connecting the control circuit to a power source. The control circuit terminates power to the heating element in response to the heating element exceeding a first temperature limit. The isolation device isolates the control circuit from the power source in response to the heating element exceeding a second temperature limit.

The second temperature limit is greater than the first temperature limit. The control circuit includes a central processing unit and a comparator interconnecting the heating element to central processing unit. The comparator proves a signal to the central processing unit in response to the heating element exceeding the first temperature limit. It is contemplated for the isolation device is a fuse. The comparator is interconnected to the fuse. The comparator causes the fuse to blow in response to the temperature of the heating element exceeding the second temperature limit. The control circuit also includes a switch interconnecting the central processing unit to the heating element. The central processing unit opens the switch in response to the heating element exceeding the first temperature limit so as to disconnect the supply of power to the heating element. The switch may be a triac.

In accordance with a further aspect of the present invention, a heating pad is provided. The heating pad includes a heating element and a control circuit operatively connected to the heating element for providing a predetermined level of power thereto. An isolation device interconnects a power source to the control circuit. The isolation device has a first open configuration preventing transmission of electrical power therethrough and a second closed configuration allowing transmission of electrical power therethrough. The control circuit terminates power to the heating element in response to the heating element exceeding a first temperature limit. The isolation device moves from the closed configuration to the open configuration in response to the heating element exceeding a second temperature limit.

The second temperature limit is greater than the first temperature limit. The control circuit includes a central processing unit and a comparator interconnecting the heating element to central processing unit. The comparator provides a signal to the central processing unit in response to the heating element exceeding the first temperature limit. It is contemplated for the isolation device to be a fuse. The comparator is interconnected to the fuse. The comparator causes the fuse to blow in response to the temperature of the heating element exceeding the second temperature limit. The control circuit also includes a switch interconnecting the central processing unit to the heating element. The central processing unit opens the switch in response to the heating element exceeding the first temperature limit so as to disconnect the supply of power to the heating element. The switch may be a triac.

The heating element includes a heating conductor operatively connected to the control circuit and a negative temperature coefficient layer surrounding the heating conductor. A positive temperature coefficient sensor conductor extends about the negative temperature coefficient layer and is operatively connected to the control circuit.

In accordance with a still further aspect of the present invention, a heating pad is provided. The heating pad includes a heating conductor and a negative temperature coefficient layer surrounding the heating conductor. A positive temperature coefficient sensor conductor having a resistance extends about the negative temperature coefficient layer. A control circuit is operatively connected to the heating conductor for supplying power thereto. An isolation device interconnects the control circuit to a power source. The isolation device has a first open configuration preventing transmission of electrical power therethrough and a second closed configuration allowing transmission of electrical power therethrough. The control circuit terminates power to the heating conductor in response to the resistance of the positive temperature coefficient sensor conductor exceeding a first threshold. The isolation device moves from the closed configuration to the open configuration in response to the shorting of the positive temperature coefficient sensor conductor to the heating conductor.

The control circuit includes a central processing unit and a comparator interconnecting the heating conductor to central processing unit. The comparator provides a signal to the central processing unit in response to the resistance of the positive temperature coefficient sensor conductor exceeding the first threshold. The isolation device may be a fuse. The comparator is interconnected to the fuse. The comparator causes the fuse to blow in response to the shorting of the positive temperature coefficient sensor conductor to the heating conductor. The control circuit also includes a switch interconnecting the central processing unit to the heating conductor. The central processing unit opens the switch in response to the resistance of the positive temperature coefficient sensor conductor exceeding a first threshold. It is contemplated for the switch to be a triac.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
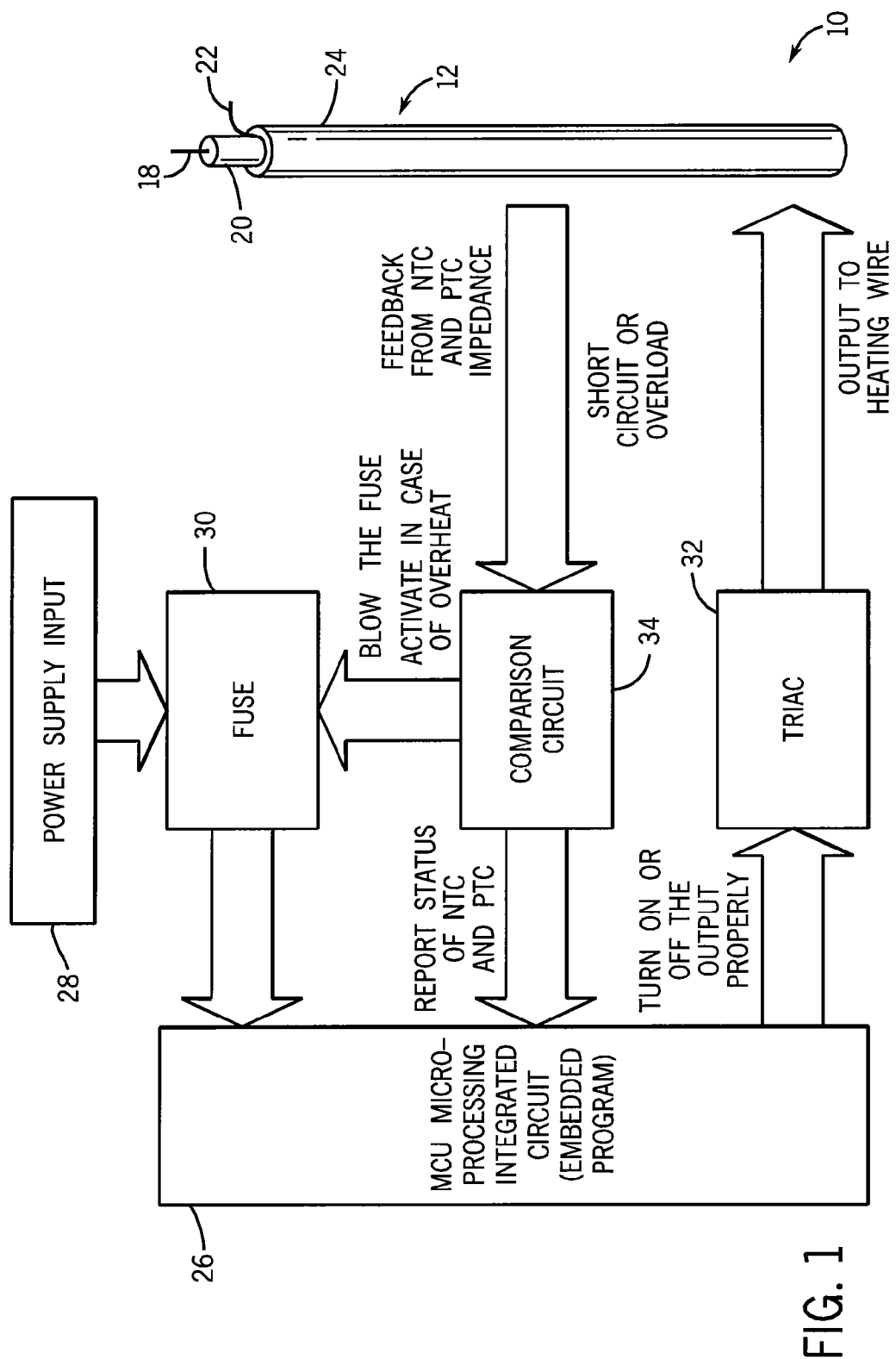
FIG. 1 is a first schematic view of a heating pad in accordance with the present invention.
Figure 3:
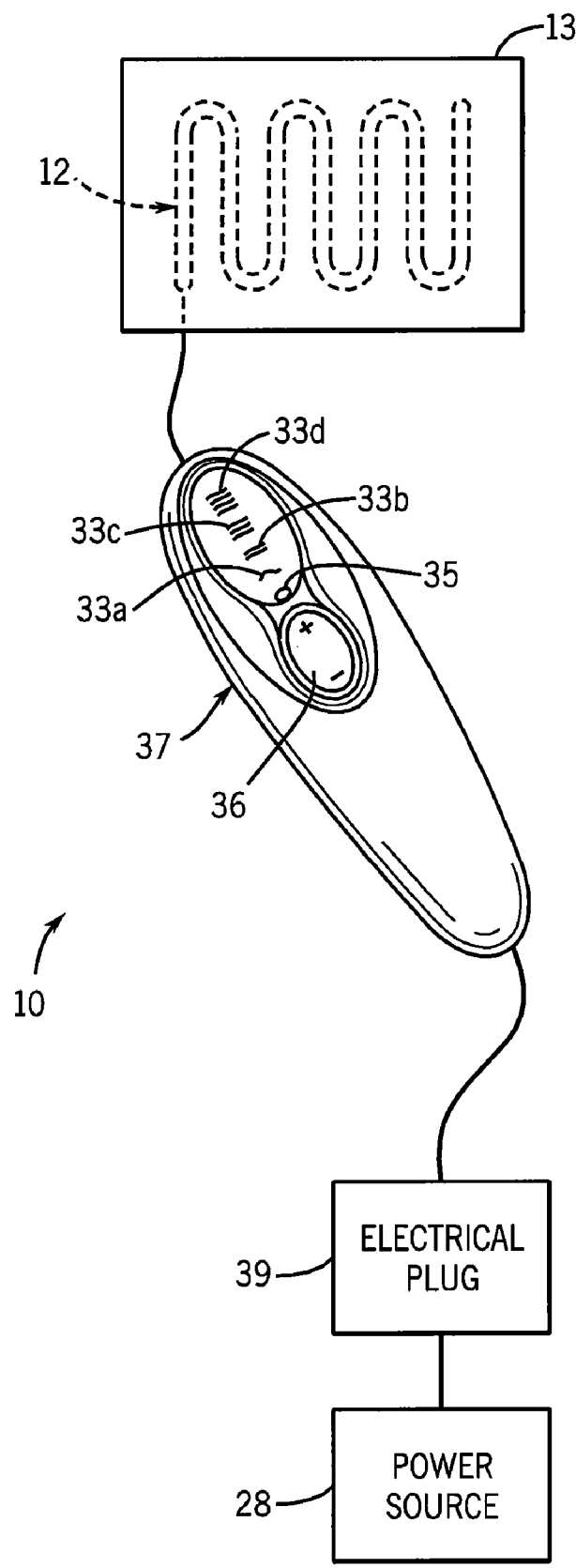
FIG. 3 is a second schematic view of the heating pad of the present invention.

Referring to FIGS. 1 and 3, a schematic view of a heating pad in accordance with the present invention is generally designated by the reference numeral 10. Heating pad 10 includes heating element 12 for heating pad 10. As is conventional, it is contemplated for heating element 12 to be received in a water-resistant outer shell and arranged in a serpentine configuration to disperse the heat generated by heating element 12. The outer shell is receiveable in one or more fabric sleeves 13 to enhance the comfort of heating pad 10 during use.

Figure 2:
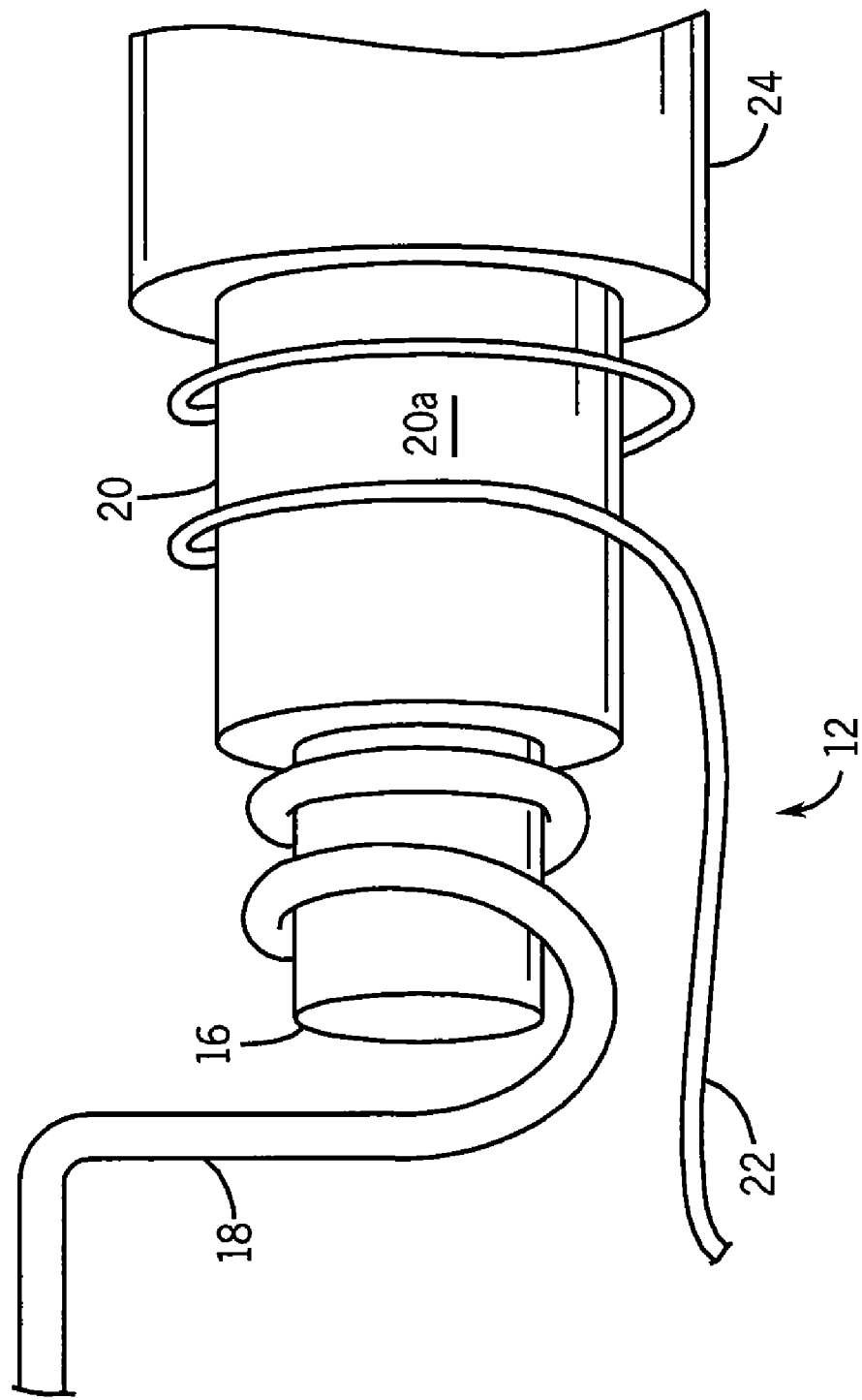
FIG. 2 is an enlarged, schematic view of a portion of a heating element for the heating pad of the present invention.

As best seen in FIG. 2, heating element 12 includes fiber core 16 fabricated from a polyester material having low electrical resistance. Heating conductor wire 18 is wound helically around fiber core 16. The alloy, gage, and turns per inch of heating conductor wire 18 are selected to provide a desired resistance per foot that produces the wattage needed for heating element 12 to a desired level. Insulating layer 20 of specially doped polyvinyl chloride (PVC) is extruded about and encapsulates heating conductor wire 18 and fiber core 16. It is contemplated for insulating layer 20 to have a negative temperature characteristic (NTC) as between temperature and resistance, such that as the temperature of insulating layer 20 increases, the resistance of insulating layer 20 decreases. Conductive sensor wire 22 is helically wound about the outer surface 20a of insulating layer 20 and waterproof, outer layer 24 is extruded about and encapsulates conductive sensor wire 22 so as to provide electrical insulation to the outside world.

Referring to FIGS. 1 and 3, heating pad 10 further includes microprocessor 26 for effectuating the methodology of the present invention, as hereinafter described. Microprocessor 26 is electrically connectable to power supply 28 though fuse 30. Output of microprocessor 26 is operatively connected to heating conductor wire 18 of heating element 12 by a switch, such as triac 32. Comparison circuit 34 is operatively connects conductive sensor wire 22 to microprocessor 26. In addition, comparison circuit 34 is operatively connected to fuse 30. It is contemplated to provide microprocessor 26, fuse 30, triac 32 and comparison circuit 34 within housing 37. It can be appreciated that the configuration of housing 37 is merely exemplary and that other configurations of housing 37 are contemplated as being with the scope of the present invention.

In operation, fuse 30 of heating pad 10 is electrically connected to power supply 28 having a predetermined voltage and frequency, e.g. 120VAC at 60 Hz, via a standard electrical plug 39. It is intended for power supply 28 to supply electrical power to microprocessor 26 and comparison circuit 34, for reasons hereinafter described. Using button 36 operatively connected to microprocessor 26, a user may select one of a plurality of settings for heating pad 12, FIG. 3. By way of example, these settings may include "ON/OFF," "WARM," "LOW," "MED" and "HIGH." Settings "WARM," "LOW," "MED" and "HIGH" have corresponding LEDs 33a-33d, respectively, associated therewith which are illuminated in response to selection by a user. In addition, controller includes power LED 35 which is illuminated in response to actuation of the heating pad 10 by a user. It is noted that other settings are possible without deviating from the scope of the present invention. Each setting corresponds to a predetermined temperature of heating pad, for example, the "WARM" setting may correspond to 110° F. (43.3° C.)+/−5%; the "LOW" setting may correspond to 120° F. (48.9° C.)+/−5%; the "MED" setting may correspond to 130° F. (54.4° C.)+/−5%; and the "HIGH" setting may correspond to 140° F. (62.8° C.)+/−5%.

Once heating pad 10 is actuated and a user-desired setting is selected by the user, microprocessor 26 actuates triac 32 such that current flows to heating conductor wire 18 so as to cause heating conductor wire 18 to radiate heat. The resistance of and leakage current flowing through conductive sensor wire 22 is monitored by comparison circuit 34 and fed back to microprocessor 26 for general temperature control. More specifically, as heretofore described, the resistance of conductive sensor wire 22 increases as the temperature of conductive sensor wire 22 increases. In response to the resistance of conductive sensor wire 22 sensed by comparison circuit 34, microprocessor 26 adjusts the current supplied to heating conductor wire 18 to maintain heating conductor wire 18 at a temperature corresponding to the user-desired setting.

As heretofore described, insulating layer 20 has a negative temperature characteristic (NTC), such that as the temperature of insulating layer 20 increases, the resistance of insulating layer 20 decreases. As the temperature of heating conductor wire 18 increases, comparison circuit 34 detects more leakage current. If the leakage current detected by comparison circuit 34 exceeds a first predetermined threshold, e.g. a leakage current corresponding 164° F., microprocessor 26 closes triac 32 and terminates the power to heating conductor wire 18. In addition, if the leakage current detected by comparison circuit 34 exceeds a second predetermined threshold, e.g. a leakage current corresponding 167° F., comparison circuit 34 causes fuse 30 to blow, thereby cutting off the electrical power to heating pad 10. It can be appreciated that, as described, heating pad 10 includes two independent circuits which provide redundant protection to prevent the overheating of heating pad 10.

Various modes of carrying out the invention are contemplated as being within the scope of the following claims particularly pointing out and distinctively claiming a subject matter which applicant regards is the invention.

I claim:

1. In a heating pad having a heating element, the improvement comprising:
a control circuit including a central processing unit operatively connected to the heating element by a switch, the central processing unit supplying current to the heating element and controlling movement of the switch between a first closed position wherein the central processing unit is electrically coupled to the heating element and an open position wherein central processing unit is isolated from the heating element
an isolation device operatively connecting the control circuit to a power source; and
a comparator operatively connected to the isolation device and interconnecting the heating element to the central processing unit, the comparator providing a signal to the central processing unit corresponding to a temperature of the heating element;
wherein:
the central processing unit adjusts the current supplied to the heating element to maintain the heating element at a desired temperature;
the central processing unit moves the switch to the open position in response to the heating element exceeding a first temperature limit; and
the isolation device isolating the control circuit from the power source in response to the heating element exceeding a second temperature limit.

2. The improvement of claim 1 wherein the second temperature limit is greater than the first temperature limit.

3. The improvement of claim 1 wherein the isolation device is a fuse.

4. The improvement of claim 3 wherein the comparator is interconnected to the fuse, the comparator causing the fuse to blow in response to the temperature of the heating element exceeding the second temperature limit.

5. A heating pad, comprising:
a heating element;
a control circuit operatively connected to the heating element by a switch, the control circuit supplying current to the heating element and controlling movement of the switch between a first closed position wherein the control circuit is electrically coupled to the heating element and an open position wherein control circuit unit is isolated from the heating element;
an isolation device interconnecting a power source to the control circuit, the isolation device having a first open configuration preventing transmission of electrical power therethrough and a second closed configuration allowing transmission of electrical power therethrough; and
a comparator operatively connected to the isolation device and interconnecting the heating element to the control circuit, the comparator providing a signal to the control circuit corresponding to a temperature of the heating element;
wherein:
the control circuit adjusts the current supplied to the heating element to maintain the heating element at a desired temperature;
the control circuit moves the switch to the open position in response to the heating element exceeding a first temperature limit; and
the comparator circuit causes the isolation device to move from the closed configuration to the open configuration in response to the heating element exceeding a second temperature limit.

6. The heating pad of claim 5 wherein the second temperature limit is greater than the first temperature limit.

7. The heating pad of claim 6 wherein the control circuit includes
a central processing unit.

8. The heating pad of claim 5 wherein the isolation device is a fuse.

9. The heating pad of claim 8 wherein the comparator is interconnected to the fuse, the comparator causing the fuse to blow in response to the temperature of the heating element exceeding the second first temperature limit.

10. The heating pad of claim 5 wherein the switch is a triac.

11. The heating pad of claim 5 wherein the heating element includes:
a heating conductor operatively connected to the control circuit by the switch;
a negative temperature coefficient layer surrounding the heating conductor; and
a positive temperature coefficient sensor conductor extending about the negative temperature coefficient layer and being operatively connected to the control circuit by the comparator.

12. A heating pad, comprising:
a heating conductor;
a negative temperature coefficient layer surrounding the heating conductor;
a positive temperature coefficient sensor conductor having a resistance and extending about the negative temperature coefficient layer;
a control circuit operatively connected to the heating conductor by a switch for supplying current to the heating conductor, the switch movable between a first open position and a second closed position;
an isolation device interconnecting the control circuit to a power source, the isolation device having a first open configuration preventing transmission of electrical power therethrough and a second closed configuration allowing transmission of electrical power therethrough; and a comparator operatively connected to the isolation device and interconnecting the positive temperature coefficient sensor to the control circuit, the comparator providing a signal to the control circuit corresponding to a temperature of the heating element;

wherein:

the control circuit adjusts the current supplied to the heating element to maintain the heating element at a desired temperature;

the control circuit moving the switch to the open position so as to terminate current to the heating conductor in response to the signal exceeding a first threshold; and the comparator moving the isolation device from the closed configuration to the open configuration in response to the shorting of the positive temperature coefficient sensor conductor to the heating conductor.

13. The heating pad of claim 12 wherein the control circuit includes
a central processing unit.

14. The heating pad of claim 12 wherein the isolation device is a fuse.

15. The heating pad of claim 14 wherein the comparator is interconnected to the fuse, the comparator causing the fuse to blow in response to the shorting of the positive temperature coefficient sensor conductor to the heating conductor.

16. The heating pad of claim 12 wherein the switch is a triac.

* * * * *